US007371830B2

(12) United States Patent
Kleiber et al.

(10) Patent No.: US 7,371,830 B2
(45) Date of Patent: *May 13, 2008

(54) METHOD FOR SEPARATING BIOLOGICAL MATERIAL FROM A FLUID USING MAGNETIC PARTICLES

(75) Inventors: Jörg Kleiber, Penzberg (DE); Thomas Walter, Bichl (DE); Herbert Harttig, Altrip (DE); Christop Lesniak, Saarbrücken (DE); Martin Mennig, Quierschied (DE); Michael Riedling, Saarbrücken (DE); Helmut Schmidt, Saarbrücken (DE)

(73) Assignee: Roche Diagnostics GmbH, Mannheim (DE)

( * ) Notice: Subject to any disclaimer, the term of this patent is extended or adjusted under 35 U.S.C. 154(b) by 362 days.

This patent is subject to a terminal disclaimer.

(21) Appl. No.: 11/041,750

(22) Filed: Jan. 24, 2005

(65) Prior Publication Data
US 2005/0266429 A1 Dec. 1, 2005

Related U.S. Application Data

(62) Division of application No. 09/756,743, filed on Jan. 10, 2001, now Pat. No. 6,870,047, which is a division of application No. 08/952,969, filed as application No. PCT/EP96/02459 on Jun. 6, 1996, now Pat. No. 6,255,477.

(30) Foreign Application Priority Data

Jun. 8, 1995 (DE) ................ 195 20 398
Oct. 12, 1995 (DE) ................ 195 37 985

(51) Int. Cl.
C07K 1/22 (2006.01)
C12N 13/00 (2006.01)
C12N 1/02 (2006.01)
C12P 19/34 (2006.01)
C12P 1/00 (2006.01)
C07H 21/00 (2006.01)

(52) U.S. Cl. ............... 530/412; 427/127; 427/212; 428/406; 428/900; 435/41; 435/91.1; 435/173.1; 435/173.9; 435/176; 435/177; 435/261; 435/814; 436/526

(58) Field of Classification Search ............ None
See application file for complete search history.

(56) References Cited

U.S. PATENT DOCUMENTS

| 2,885,366 A | 5/1959 | Iler |
| 2,913,419 A | 11/1959 | Alexander |
| 4,082,905 A | 4/1978 | Stephan et al. |
| 4,124,385 A | 11/1978 | O'Horo |
| 4,124,735 A | 11/1978 | O'Horo |
| 4,126,437 A | 11/1978 | O'Horo |
| 4,233,169 A | 11/1980 | Beall et al. |
| 4,280,918 A | 7/1981 | Homola et al. |
| 4,309,459 A | 1/1982 | Tokuoka |
| 4,336,310 A | 6/1982 | Okuyama et al. |
| 4,360,441 A | 11/1982 | Borrelli et al. |
| 4,395,271 A | 7/1983 | Beall et al. |
| 4,554,088 A | 11/1985 | Whitehead et al. ...... 252/62.54 |
| 4,564,537 A | 1/1986 | Austin et al. |
| 4,628,037 A | 12/1986 | Chagnon et al. |
| 4,672,040 A | 6/1987 | Josephson |
| 4,683,195 A | 7/1987 | Mullis et al. |
| 4,683,202 A | 7/1987 | Mullis et al. |
| 4,695,392 A | 9/1987 | Whitehead et al. |
| 4,695,393 A | 9/1987 | Whitehead et al. |
| 4,698,302 A | 10/1987 | Whitehead et al. |
| 4,699,717 A | 10/1987 | Riesner et al. |
| 4,751,211 A | 6/1988 | Fleming |
| 4,767,670 A | 8/1988 | Cox et al. |
| 4,804,561 A | 2/1989 | Tanioka et al. |
| 4,824,712 A * | 4/1989 | Falleroni et al. ............ 428/137 |

(Continued)

FOREIGN PATENT DOCUMENTS

| CA | 2223821 | 6/1996 |
| DE | 43 07 262 A1 | 9/1994 |
| DE | 195 20 964 | 12/1996 |
| DE | 195 37 985 A1 | 4/1997 |

(Continued)

OTHER PUBLICATIONS

BioRobot 9600 "The BioRobot 9600—An integrated, compact workstation for nucleic acid purification", Qiagen Product Guide (1997) 100-103.
Ishida et al., "Development on full automatic DNA, RNA and Plasmid Extraction Instrument Using Unique Magnetic Particles Isolation Technology", Toyobo Product Information, unknown.
Merel et al., "Completely automated extraction of DNA from whole blood", Clin Chem, (1996) 1285-6.

(Continued)

*Primary Examiner*—David M. Naff
(74) *Attorney, Agent, or Firm*—Olga Kay; Townsend and Townsend and Crew, LLP

(57) ABSTRACT

Magnetic particles are prepared containing a magnetic core coated with a glass layer having a substantially pore-free glass surface or having pores with a diameter of less than 10 nm. The particles are used for separating biological material such as nucleic acids. A preferred process of preparing the particles is by forming a mixture of magnetic cores with a sol formed from an alcohol and a metal alkoxide, spray-drying the mixture to coat the cores with a layer of gelled sol, and heating the coated cores to obtain the magnetic glass particles. Preferably, the particles have an average particle size of less than 100 μm. The magnetic core may be a composite material containing a mica core and magnetite particles immobilized on the mica core, and the glass layer may contain boron oxide. Magnetic core materials include magnetite ($Fe_3O_4$) and $Fe_2O_3$.

4 Claims, 3 Drawing Sheets

U.S. PATENT DOCUMENTS

| | | | |
|---|---|---|---|
| 4,910,148 A | | 3/1990 | Sorensen et al. |
| 5,039,559 A | | 8/1991 | Sang et al. |
| 5,055,194 A | | 10/1991 | Goetz et al. |
| 5,057,426 A | | 10/1991 | Henco et al. |
| 5,075,430 A | | 12/1991 | Little |
| 5,076,950 A | | 12/1991 | Ullman et al. |
| 5,155,018 A | | 10/1992 | Gillespie et al. ............... 435/91 |
| 5,206,568 A | | 4/1993 | Björnson et al. |
| 5,210,015 A | | 5/1993 | Gelfand et al. |
| 5,217,804 A | | 6/1993 | James et al. |
| 5,234,809 A | | 8/1993 | Boom et al. |
| 5,236,623 A | | 8/1993 | Chevallier |
| 5,279,936 A | | 1/1994 | Vorpahl |
| 5,312,485 A | | 5/1994 | Wason et al. |
| 5,316,699 A | | 5/1994 | Ritter et al. |
| 5,340,393 A | | 8/1994 | Jacobson |
| 5,346,994 A | | 9/1994 | Chomczynski |
| 5,368,933 A | | 11/1994 | Aoki et al. |
| 5,389,482 A | | 2/1995 | Okano et al. |
| 5,395,498 A | | 3/1995 | Gombinsky et al. |
| 5,438,127 A | | 8/1995 | Woodard et al. |
| 5,443,791 A | | 8/1995 | Cathcart et al. |
| 5,458,813 A | * | 10/1995 | Palladino ..................... 516/98 |
| 5,470,660 A | | 11/1995 | Misawa et al. |
| 5,487,972 A | | 1/1996 | Gelfand et al. |
| 5,503,816 A | * | 4/1996 | Woodard et al. ............ 423/304 |
| 5,512,332 A | | 4/1996 | Liberti et al. |
| 5,512,405 A | | 4/1996 | Misawa et al. |
| 5,520,899 A | | 5/1996 | Woodard et al. |
| 5,578,238 A | | 11/1996 | Weiss et al. |
| 5,582,988 A | | 12/1996 | Backus et al. |
| 5,597,531 A | | 1/1997 | Liberti et al. |
| 5,599,627 A | | 2/1997 | Aoki et al. |
| 5,610,274 A | | 3/1997 | Wong |
| 5,648,170 A | | 7/1997 | Okano et al. |
| 5,658,548 A | * | 8/1997 | Padhye et al. ............... 423/335 |
| 5,660,984 A | | 8/1997 | Davis et al. |
| 5,662,824 A | | 9/1997 | Sang et al. |
| 5,665,554 A | | 9/1997 | Reeve et al. |
| 5,681,946 A | | 10/1997 | Reeve |
| 5,683,875 A | | 11/1997 | Lichtenwalter |
| 5,693,502 A | | 12/1997 | Gold et al. |
| 5,693,785 A | | 12/1997 | Woodward et al. |
| 5,698,271 A | | 12/1997 | Liberti et al. |
| 5,705,137 A | | 1/1998 | Goerl et al. |
| 5,723,591 A | | 3/1998 | Livak et al. |
| 5,734,020 A | | 3/1998 | Wong |
| 5,747,663 A | | 5/1998 | Colpan et al. |
| 5,763,173 A | | 6/1998 | Gold et al. |
| 5,783,686 A | | 7/1998 | Gonzalez |
| 5,804,375 A | | 9/1998 | Gelfand et al. |
| 5,898,071 A | | 4/1999 | Hawkins |
| 5,904,848 A | | 5/1999 | Wong et al. |
| 5,925,573 A | | 7/1999 | Colin et al. |
| 5,928,958 A | | 7/1999 | Pilgrimm |
| 5,945,525 A | | 8/1999 | Uematsu et al. |
| 5,972,721 A | | 10/1999 | Bruno et al. |
| 5,990,301 A | | 11/1999 | Colpan et al. |
| 5,990,479 A | | 11/1999 | Weiss et al. |
| 6,136,083 A | | 10/2000 | Schmidt et al. |
| 6,255,477 B1 | * | 7/2001 | Kleiber et al. ............. 536/25.4 |
| 6,274,386 B1 | | 8/2001 | Hartig |
| 6,296,937 B2 | | 10/2001 | Pryor et al. |
| 6,368,800 B1 | | 4/2002 | Smith et al. |
| 6,545,143 B1 | | 4/2003 | Harttig et al. |
| 6,870,047 B2 | * | 3/2005 | Kleiber et al. ............. 536/25.4 |
| 6,919,444 B2 | | 7/2005 | Harttig |

| | | |
|---|---|---|
| 2003/0096984 A1 | 5/2003 | Cully et al. |

FOREIGN PATENT DOCUMENTS

| | | |
|---|---|---|
| EP | 0 937 497 A2 | 12/1988 |
| EP | 0 343 934 A3 | 11/1989 |
| EP | 0 389 063 A3 | 9/1990 |
| EP | 0 125 995 | 11/1991 |
| EP | 0 652 490 | 5/1995 |
| EP | 0 757 106 A2 | 5/1997 |
| EP | 0 811 694 | 10/1997 |
| EP | 0 866 071 A2 | 3/1998 |
| EP | 1 281 714 B1 | 2/2003 |
| EP | 05004214.2 | 10/2005 |
| JP | 5281778 | 10/1993 |
| JP | 7235407 | 9/1995 |
| JP | 9327290 | 12/1997 |
| JP | 9327291 | 12/1997 |
| WO | WO 83/03363 | 10/1983 |
| WO | WO 88/06633 | 9/1988 |
| WO | WO 89/01035 | 2/1989 |
| WO | WO 91/02811 | 3/1991 |
| WO | WO 91/15768 A1 | 10/1991 |
| WO | WO 92/02638 | 2/1992 |
| WO | WO 93/10162 | 5/1993 |
| WO | WO 91/12079 | 8/1994 |
| WO | WO 95/04140 | 2/1995 |
| WO | WO 95/06652 | 3/1995 |
| WO | WO 96/03653 | 2/1996 |
| WO | WO 96/11054 | 4/1996 |
| WO | WO 96/41811 | 12/1996 |
| WO | WO 96/41840 | 12/1996 |
| WO | WO 97/10331 | 3/1997 |
| WO | WO 97/10359 | 3/1997 |
| WO | WO 97/29825 | 8/1997 |
| WO | WO 98/31461 | 7/1998 |
| WO | WO 98/31480 | 7/1998 |
| WO | WO 99/16781 | 4/1999 |
| WO | WO 99/26605 | 6/1999 |
| WO | WO 00/32762 | 11/1999 |
| WO | WO 99/67371 | 12/1999 |
| WO | WO 00/37291 | 5/2001 |

OTHER PUBLICATIONS

Alderton et al., "Magnetic Bead Purification of MI3 DNA Sequencing Templates," Analytical Biochemistry, vol. 201, 166-169, 1992.

Chou et al., "Prevention of pre-PCR MIS-Priming and Primer Dimerization Improves Low-Copy-Number Amplifications," Nucleic Acids Research, vol. 20, No. 7, 1717-1723, 1992.

Dang et al., "Oligonucleotide Inhibitors of Taq DNA Polymerase Facilitate Detection of Low Copy Number Targets by PCR," JMB, vol. 264, 268-278, 1996.

Jakobi et al., "Filter-Supported Preparation of γ Phage DNA," Analytical Biochemistry, vol. 175, 196-201, 1988.

Marko et al., "A Procedure for The Large-Scale Isolation of Highly Purified Plasmid DNA Using Alkaline Extraction and Binding to Glass Powder," Analytical Biochemistry, vol. 121, 382-387, 1982.

Scalice et al., "Monoclonal Antibodies Prepared Against the DNA Polymerase From *Thermus aquaticus* are Potent Inhibitors of Enzyme Activity," Journal of Immunological Methods, vol. 172, 147-163, 1994.

Vogelstein et al., "Preparative and Analytical Purification of DNA from Agarose," Proc. Natl. Acad. Sci, USA, vol. 76, No. 2, 615-619, 1979.

Boom et al., J. Clin, Microbiol. 28:495-503 (1990).

Chapter 2 (DNA) and Chapter 4 (RNA) of P. Ausubel et al., eds., Current Protocols in Molecular Biology, Wiley-Interscience, New York (1993).

Chen et al., Anal. Biochem. 101:339-341 (1980).

Kirk-Othmer Encyclopedia of Chemical Technology, Fourth Edition, vol. 6, pp. 773-775, 1993.

Wirth et al., Science 275:44-47 (1997).

Database CAS online, AN 126:182277, Uematsu et al. "Magnetic carriers for the separation of nucleic acids and methods of using them". Jpn. Kokai Tokkyo Koho, 9 pp. Jan. 21, 1997, abstract (EP 0 757 106 A2 corresponding thereto in English is enclosed).

Database CAS online, AN 126:86772, Kleiber et al. "Magnetic particles and their use for isolation of biological materials". Ger. Offen., 9 pp. Dec. 12, 1996, abstract.

Bischoff et al., "Nucleic Acid Resolution by Mixed-Mode Chromatography", J. Chromatog. (1984) 296:329-337.

Crowther et al., "High Performance Liquid Chromatographic Separation of Oligonucleotides and Other Nucleic Acid Constituents on Multifunctional Stationary Phases", J. Chromatog. (1983) 282:619-628.

Edwardson et al., "Separation and purification of oligonucleotides using a new bonded-phase packing material", J. Chromatog. (1991) 545:79-89.

Kirk-Othmer Encyclopedia of Chemical Technology, (1997) Fourth Edition, vol. 21, pp. 1021-1022.

Macherey-Nagel, Macherey-Nagel homepage on the Internet on Jul. 9, 2003, at http://www.macherey-nagel.com.

McLaughlin, L., "Mixed-Mode Chromatography of Nucleic Acids", Chem Rev (1989) 89: 309-319.

Northrop et al., "Preparation and Evaluation of a Bimodal Size-Exclusion Chromatography Column Containing a Mixture of Two Silicas of Different Pore Diameter", Anal. Chem. (1991) 63:1350-1354.

Promega, Technical Bulletin No. 292 Wizard .RTM. Plus Series 9600 .TM. DNA Purification System, (Promega Corp.) (Sep. 1998).

Promega, Technical Bulletin No. 225 Wizard .RTM. Plus SV Minipreps DNA Purification System, (Promega Corp.) (Sep. 1999).

Promega, Technical Bulletin No. 259 Wizard .RTM. PureFection Plasmid DNA Purification System, (Promega Corp.) (Sep. 1999).

QuantiBlot, QuantiBlot Human DNA Quantitation System, PE Applied Biosystems, Feb. 5, 1996, pp. 1-5 (http://ww.pebio.com/fo/773503/773503.html).

* cited by examiner

1 μg λ DNA    V38/2        V38/3        V38/4
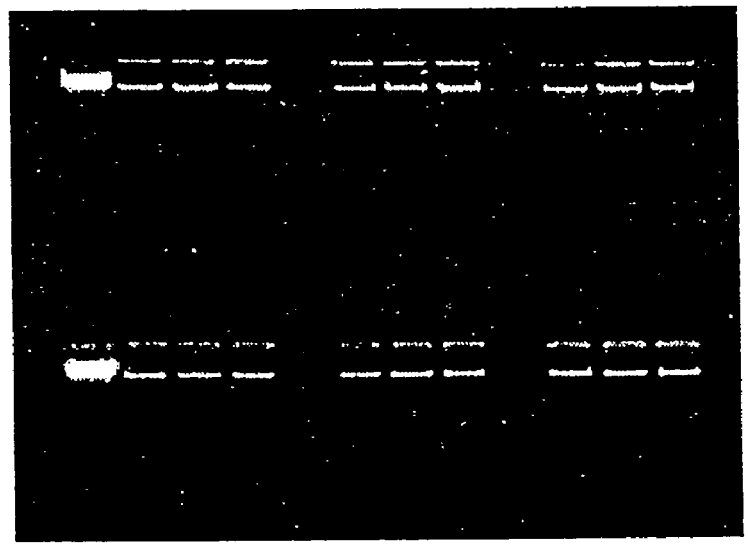
FIG 2
MWM III V38/2    | 38/3    |    V38/4
2   3   1   2   3   1   2   3
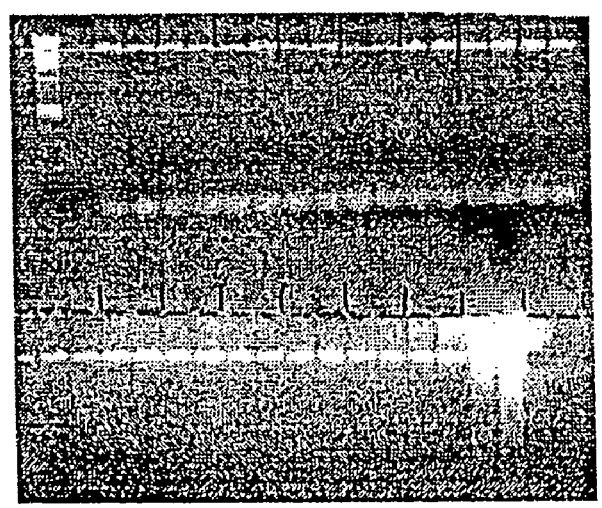
15 kb
15 kb
1   2   1   2   3   1   2   K
V38/2    |    V38/3    |    V38/4        FIG 3 nd# METHOD FOR SEPARATING BIOLOGICAL MATERIAL FROM A FLUID USING MAGNETIC PARTICLES

This application is a divisional of U.S. application Ser. No. 09/756,743, filed Jan. 10, 2001, now U.S. Pat. No. 6,870,047, which is a divisional of U.S. application Ser. No. 08/952,969, filed Mar. 11, 1998 now U.S. Pat. No. 6,255,477, issued Jul. 3, 2001, which is a 35 U.S.C. §371 national phase filing of International Application No. PCT/EP96/02459, which was filed with the Patent Cooperation Treaty on Jun. 6, 1996, and is entitled to priority under 35 U.S.C. §119 to German Patent Applications 19537985.3, filed Oct. 12, 1995 and 19520 398.4, filed Jun. 8, 1995, all of which are incorporated herein by reference.

BACKGROUND OF THE INVENTION

1. Field of the Invention

Subject matter of the invention are magnetic particles having a glass surface, and a procedure for purifying a biological material, especially nucleic acids, using glass particles in the presence of chaotropic salts. Yet another subject matter of the invention is a procedure for isolating these biological materials and a procedure for concentrating biological materials and transferring them from solutions having a high concentration of salts to solutions having a low concentration of salts.

2. Description of the Related Art

Many biological materials, especially nucleic acids, present special challenges in terms of isolating them from their natural environment. On the one hand they are often present in very small concentrations and, on the other, they are often found in the presence of many other solid and dissolved substances that make them difficult to isolate or measure.

For this reason, many procedures and materials for isolating nucleic acids from their natural environment have been proposed in recent years. In Proc. Natl. Acad. USA 76, 615-691 (1979), for instance, a procedure for binding nucleic acids in agarose gels in the presence of sodium iodide in ground flint glass is proposed.

The purification of plasmid DNA from bacteria on glass dust in the presence of sodium perchlorate is described in Anal. Biochem. 121, 382-387 (1982).

In DE-A 37 34 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a menthol-containing buffer in Tris/EDTA buffer.

A similar procedure for purifying DNA from lambda phages is described in Anal. Biochem. 175, 196-201 (1988).

The procedure known from the prior art entails the selective binding of nucleic acids to glass surfaces in chaotropic salt solutions and separating the nucleic acids from contaminants such as agarose, proteins or cell residue. To separate the glass particles from the contaminants according to the prior art, the particles are either centrifuged or fluids are drawn through glass fiber filters. This is a limiting step, however, that prevents the procedure from being used to process large quantities of samples.

The use of magnetic particles to immobilize nucleic acids after precipitation by adding salt and ethanol is described in Anal. Biochem. 201, 166-169 (1992) and PCT GB 91/00212. In this procedure, the nucleic acids are agglutinated along with the magnetic particles. The agglutinate is separated from the original solvent by applying a magnetic field and performing a wash step. After one wash step, the nucleic acids are dissolved in a Tris buffer. This procedure has a disadvantage, however, in that the precipitation is not selective for nucleic acids. Rather, a variety of solid and dissolved substances are agglutinated as well. As a result, this procedure can not be used to remove significant quantities of any inhibitors of specific enzymatic reactions that may be present.

A porous glass in which magnetic particles are embedded is described in U.S. Pat. No. 4,233,169.

Magnetic, porous glass is also available on the market that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin.

SUMMARY OF THE INVENTION

The task of the invention was to provide better materials for immobilizing biological materials and a simple procedure for isolating biological materials, especially nucleic acids, that is also suitable for use in routine diagnostic procedures.

Subject matter of the invention are magnetic particles with an outer glass surface that is substantially pore-free, or that has pores with less than 10 nm diameter. Yet another subject matter of the invention are ferromagnetic particles having a glass surface, a procedure for isolating biological materials, especially nucleic acids, and a procedure for the manufacture of magnetic glass particles.

BRIEF DESCRIPTION OF THE DRAWINGS

FIG. 2 illustrates the separation of isolated nucleic acids according to the invention in an agarose gel.

FIG. 3 depicts the separation of reaction products after isolation according to the invention and amplification by means of PCR

DETAILED DESCRIPTION OF THE INVENTION

Figure 1:
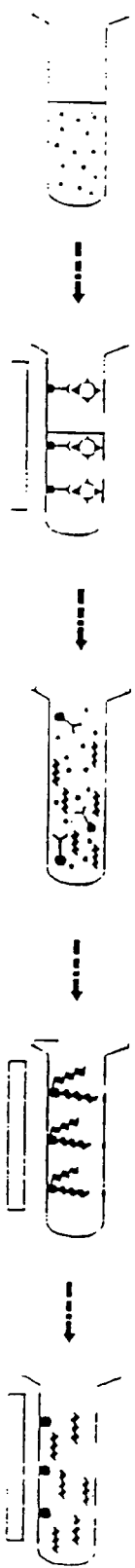
FIG. 1 illustrates the isolation of nucleic acids from a sample containing cells.

Particles, according to the expert, are solid materials having a small diameter. Particles like these are often also referred to as pigments. According of the present invention, those particles are especially suited that have an average particle size of less than 100 µm. More preferably they have an average particle size of between 10 and 60 µm. The distribution of particle size is preferably relatively homogeneous. In particular, there are almost no particles <10 µm or >60 µm in size.

Those materials are referred to as magnetic that are drawn to a magnet, i.e., ferromagnetic or superparamagnetic materials, for instance. In addition, those materials that are called softly magnetic are also understood to be magnetic, e.g., ferrites. Especially preferred according to the present invention are ferromagnetic materials, especially if they have not yet been premagnetized. Premagnetization in this context is understood to mean bringing in contact with a magnet, which increases the remanence. Especially preferred are ferromagnetic materials, such as magnetite ($Fe_3O_4$) or $Fe_2O_3$.

An outer surface of a particle is understood to mean the contiguous surface from which perpendicular lines can be drawn outwards towards the particle's environment that do not cut through the particle itself.

A pore is understood to be a recess in the outer surface of the particle. The surface reaches so far into the particle that a perpendicular line drawn in the recess on the surface cuts the particle at least once in the direction of the adjacent environment of the particle. In addition, pores reach into the particle to a depth that is greater than one radius of the pore.

A glass according to the present invention is understood to be an amorphous material that contains silicium. Glass can contain other materials such as

| | |
|---|---|
| $B_2O_3$ | (0-30%) |
| $Al_2O_3$ | (0-20%) |
| CaO | (0-20%) |
| BaO | (0-10%) |
| $K_2O$ | (0-20%) |
| $Na_2O$ | (0-20%) |
| MgO | (0-18%) |
| $Pb_2O_3$ | (0-15%) |

Glass can also contain a smaller percentage (0-5%) of a number of other oxides such as $Mn_2O_3$, $TiO_2$, $As_2O_3$, $Fe_2O_3$, CuO, CoO, etc. Surfaces made of a composition of borosilicate glass, flint glass or silica have proven to be especially effective. Borosilicate glasses, which are especially preferred in terms of nucleic acid yield, have a boroxide content of more than 25%. A glass having a 70/30 composition of $SiO_2/B_2O_3$ is especially preferred. Especially preferred according to the present invention are glasses that are formed using the gel sol process and then dried and compressed. The basic principles of this process are known and were described, for instance, in C. J. Brinker, G. W. Scherer "Sol Gel Science—The Physics and Chemistry of Sol Gel Processing", Academic Press Inc. 1990, Sol-Gel Optics, Processing and Applications, Lisa C. Klein, Ed., Kluwer Academic Publishers 1994, p. 450 ff., and in DE-A-1941191, DE-A-3719339, DE-A4117041 and DE-A4217432. The principle has not been described for magnetic particles to date, however. The fact that the process could be used to create magnetic particles that have very surprising characteristics when used to isolate biological materials, especially nucleic acids, was not expected. In the gel-sol process, alkoxides of network-forming components, e.g., $SiO_2$, $B_2O_3$, $Al_2O_3$, $TiO_2$, $ZrO_2$, $GeO_2$, are combined with oxides and salts of other components, e.g., in an alcohol solution, and then hydrolized. The equation below describes the procedure for making sodium boroaluminium silicate glass:

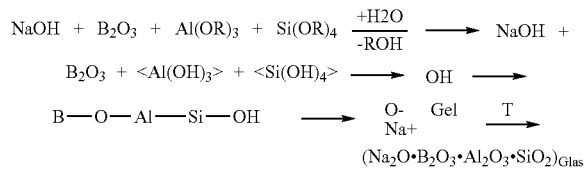

Water is added to begin the hydrolysis process of the starting components. The reaction proceeds relatively quickly because the alkali ions have a catalytic effect on the speed of hydrolysis of the silicic acid ester. Once the gel is formed it can be dried and densified by means of a thermal process to form glass.

The sol:pigment ratio has a considerable effect on the yield of magnetic pigments provided by this invention. The ratio is limited by the fact that the portion of pigment must be so small that the mass created can still be pumped or sprayed. If the portion of the pigment is too small, the fine portion, e.g., of non-magnetic material, becomes too great and causes interference. Ratios of 10 to 25 g pigment: 100 ml sol were found to be useful in terms of pigment yield.

To create a powder, the slurry is preferably sprayed through a nozzle and the aerosol is dried as it falls. The nozzle is preferably heated to speed up the drying of the slurry. Depending on the nozzle geometry, the nozzle temperature is preferably from 120 to 200° C. A compromise is found by utilizing a sufficient evaporation speed but avoiding overheating.

To optimize the yield, the densification temperature should be as high as possible. If it is too high, however, the particles will stick together and form agglomerates that must be sieved out. Additional treatment of the particles in at too high temperature will result in a loss of magnetic properties. Too high temperatures should therefore be omitted.

A substantially pore-free surface is understood to mean a surface with pores (as described above) covering less than 5%, but preferably less than 2%, and especially preferred, less than 0.1% of its area. If pores are present, they preferably have a diameter of less than 10 nm and, especially preferred, 1 nm.

Especially preferred according to the present invention are particles that contain a mica core coated with $TiO_2$ and magnetite particles immobilized on it. In this design, the composite material formed is surrounded by the glass layer. Both the core and the magnetite particles are crystalline and non-porous. The spaces on the surface of the mica that are not occupied by the magnetite particles are covered by a glass layer that is thicker than at the tips of the magnetite particles, basically resulting in a non-porous glass surface.

The non-porosity of the magnetic particles is based only on the outer surface and not on the inside of the particle. The particle can therefore be porous on the inside only if the surface is enclosed by a substantially pore-free glass or a glass surface having pores with a diameter of less than 10 nm.

Surprisingly, the magnetic particles provided by the invention are especially suited for isolating biological materials from samples. Long nucleic acids in particular are not destroyed—or only minimally—when they are immobilized on them. In addition, the core material is a natural resource and therefore causes little ecological concern. Moreover, the particles according to the invention are inexpensive and easy to manufacture.

Yet another object of the invention are ferromagnetic particles having a glass surface. Superparamagnetic particles are described in the prior art. It has been demonstrated that ferromagnetic particles covered with a glass surface offer considerable advantages for isolating biological materials. If the ferromagnetic particles have not been brought in contact with a magnetic field, gravity is the only force that can cause them to sediment out. They can be resuspended easily and quickly by shaking the solution. The sedimentation procedure that does not utilize a magnetic field preferably proceeds more slowly than the immobilization of biological materials on the surface of the particles. This is especially true for nucleic acids. The ferromagnetic particles can be easily collected at a specific location in the sample fluid by means of a magnet. The fluid is then separated from the particles and, therefore, from the immobilized biological materials.

The glass surface of the ferromagnetic particles provided by the invention can be pore-free or contain pores. For the reasons given above for the magnetic particles provided by the invention, it is preferable for the outer surface of the ferromagnetic particles to also be substantially pore-free or to have pores with a diameter of less than 10 nm. The ferromagnetic particles provided by the invention also preferably have a particle size of between 10 and 60 µm, and especially preferred, of between 20 and 50 µm. Especially preferred are particles with surface pores (if present) having a diameter of less than 10 nm and, especially preferred, 1 nm. An example of a ferromagnetic particle according to the invention is the composite material described above which is made of mica and magnetite particles surrounded by a glass layer.

Yet another object of the invention is a procedure for isolating a biological material by
   bringing a sample containing the biological material in a fluid in contact with the magnetic particles according to the invention or the ferromagnetic particles according to the invention under conditions in which the biological material binds to the particle surface, and
   separating the biological material from the fluid.

Biological materials are understood to mean materials with a particular or molecular basis. They include, in particular, cells such as viruses or bacteria, as well as isolated human and animal cells such as leucocytes, and immunologically active low and high molecular chemical compounds such as haptens, antigens, antibodies and nucleic acids. Nucleic acids such as DNA or RNA are especially preferred.

Samples according to the invention include clinical samples such as blood, serum, oral rinses, urine, cerebral fluid, sputum, stool, biopsy specimens and bone marrow samples. The sample can also be of a type used for environmental analysis, food analysis or molecular biology research, e.g., from bacterial cultures, phage lysates and products of amplification procedures such as the PCR.

The particles according to the invention have an inner core to which the outer glass surface is applied. The core can be a composite material, or it can be a simple iron core. The core can also consist of a crystalline, ceramic or glass-like structure in which iron oxide is embedded.

The procedure described can be used to isolate native or modified biological material. Native biological material is understood to be material, the structure of which was not irreversibly changed compared with the naturally-occurring biological materials. This does not mean that other components of the sample can not be modified, however. If cells are isolated, for example, the medium surrounding the cells can be modified, but not the cells themselves. If nucleic acids are isolated, they should be cut or modified in their native form, i.e., non-denatured, not cut or not modified by coupling them with reactive groups. The concept of native biological material therefore does not encompass biotinylated nucleic acids in particular. Examples of native biological materials are phage DNA or cellular nucleic acids from blood.

Modified biological materials include materials that do not occur in nature, e.g., nucleic acids that are modified by attaching to them groups that are reactive, detectable or capable of immobilization. An example of this are biotinylated nucleic acids.

In certain cases the sample can be used without pretreatment in the isolation procedure according to the invention. In many cases, however, the sample should be lysed using an appropriate method, releasing the biological material contained in the sample. Procedures for lysing samples are known by the expert and can be chemical, enzymatic or physical in nature. A combination of these procedures is applicable as well. For instance, lysis can be performed using ultrasound, high pressure, by shear forces, using alkali, detergents or chaotropic saline solutions, or by means of proteinases or lipases.

With regard for the lysis procedure to obtain nucleic acids, special reference is made to Sambrook et al.: Molecular Cloning, A Laboratory Manual, 2nd Addition, Cold Spring Harbour Laboratory Press, Cold Spring Harbour, NY and Ausubel et al.: Current Protocols in Molecular Biology 1987, J. Viley and Sons, NY.

In addition to the biological material to be isolated, the sample can also contain other components in a fluid such as cell residue, proteins, salts and other substances that are not to be isolated. This sample, which preferably contains the biological material in native form, is brought in contact with the particles under conditions in which the target biological material binds to the particle surface. The conditions for this depend on the type of biological material involved, but are basically known. They also depend on the method by which the biological material is bound to the surface. If immunological interactions are utilized for the binding, for instance, conditions must be selected that are suitable for the formation of immunocomplexes. If modified nucleic acids are used, the binding can take place via the groups of nucleic acids that represent the modification, e.g., biotin via binding with streptavidin-coated surfaces. With nucleic acids in particular, however, a direct binding of nucleic acids to glass is preferred because among other reasons the nucleic acids do not have to be modified and even native nucleic acids can be bound. The procedure for binding native nucleic acids to glass particles can be analogous to the procedure described in the prior art. It is preferably performed in the presence of chaotropic salts with a concentration of between 2 and 8 mol/l, and preferably between 4 and 6 mol/l. Chaotropic salts can be sodium iodite, sodium perchlorate, guanidinium thiocyanate, guanidinium isothiocyanate or guanidinium hydrochlorite. Other compounds are also possible.

To bring the sample in contact with the particles, the sample is mixed with the particles and incubated for a period of time sufficient for the binding to occur. Experts are usually familiar with the duration of the incubation step from procedures for performing treatment with non-magnetic particles. This step can be optimized by determining the quantity of immobilized biological material on the surface at different points in time. Incubation times of between 10 seconds and 30 minutes can be appropriate for nucleic acids.

Depending on the size and type of magnetic particles, the particles either separate out of the fluid during the incubation period itself or the suspension remains intact for a longer period of time. If the particles are very small and superparamagnetic, the suspension remains intact for a longer period of time. If the particles are of larger size, the particles slowly separate out of the fluid during the incubation period. Aggregates of this nature form in particular when ferromagnetic particles are involved. When the ferromagnetic particles are not premagnetized, as is preferred, a very gentle separation is guaranteed.

Immobilization is preferably not performed via precipitation by lowering the solubility of the materials to be immobilized. Rather, immobilization is based on biospecific interactions (capture molecules) or adsorption. This largely prevents contaminants from being non-specifically included.

After incubation, the biological material is separated from the fluid. This is achieved in general by separating the material bound to the magnetic particles using a magnetic field. For instance, the magnetic particles can be pulled to the wall of the vessel in which incubation was performed. The fluid containing the sample contents that were not bound to the magnetic particles can then be removed. The removal procedure used depends on the type of vessel in which incubation was performed. Suitable steps include removing the fluid via pipetting or aspiration.

The magnetic particles can then be purified one or more times using a wash solution, if desired. A wash solution is used that does not cause the biological material to be deliberated from the particle surface but that washes away the undesired contaminants as thoroughly as possible. This wash step preferably takes place by incubating the wash solution with the particles. The particles are preferable resuspended during this step, e.g., by means of shaking or applying a magnetic field that is not identical to the first magnetic field. The contaminated wash solution is preferably separated just like the sample in the step described above for binding the biological material.

After the last wash step, the magnetic particles can be dried briefly in a vacuum, or the fluid can be allowed to evaporate. A pretreatment step using acetone may also be performed.

If desired, the biological material purified in this manner can be separated from the magnetic particles. This step also depends on the manner in which the biological material was bound to the magnetic particles. If the biological material is native nucleic acids and the magnetic particles are glass-coated particles, the nucleic acids can be removed from the particles according to the invention using an elution buffer having a low salt content. Buffers of this nature are known from DE 3724442 and Analytical Biochemistry 175, 196-201 (1988). The elution buffers with a low salt content are in particular buffers with a content of less than 0.2 mol/l. In an especially preferred embodiment, the elution buffer contains Tris. In another special embodiment, the elution buffer is demineralized water.

In yet another embodiment, the purification and isolation procedure described is performed after the cells (e.g., viral particles or prokaryotic or eukaryotic cells) are separated immunomagnetically from a bodily fluid or tissue. In this step, the sample is incubated, e.g., while shaking, with magnetic particles to which an antibody against an antigen on the cell is immobilized. These particles can be particles according to the invention or commercially available particles (e.g., MACS Microbreads from Miltenyi Biotec GmbH, Bergisch Gladbach, Germany). After a magnetic field is applied, one or more wash steps are performed using a saline solution. Particles are obtained to which the desired cells are bound. The bound cells are then resuspended in a saline buffer. In a preferred embodiment, this saline buffer is a chaotropic saline solution so that the nucleic acids contained in the cell are released from the cells.

An especially advantageous procedure for isolating nucleic acids from samples containing cells is achieved by combining the isolation of cells described above with the isolation of nucleic acids—preferable in their native form—also described above, on the magnetic particles according to the invention. The advantage of this embodiment is its potential simplicity (single-tube method), high sensitivity (especially important in medical microbiology and oncology), and the ease with which it can be automated.

The biological materials isolated using the procedure according to the invention can now be used further as necessary. For instance, they can be used as a substrate for various enzymatic reactions. When nucleic acids are involved, they can be used for sequencing, radioactive or non-radioactive labelling, amplification of one or more of the sequences they contain, transcription, hybridization with labelled probe nucleic acids, translation or ligation. An advantage of the procedure according to the invention is that it is very easy to separate the biological material from the fluid. In the prior art, a centrifugation step was used to separate the glass particles from contaminants, or, when the biological material is bound to glass fiber filters the fluid is drawn through the filters. This is a limiting step that makes it difficult to process large quantities of sample.

The biological materials can be separated from contaminants more effectively using the particles according to the invention. In particular, inhibitors for certain enzymatic reactions can be removed to a large extent according to the invention. The yield of biological material is relatively high. Fractionation of long nucleic acids was not observed. The particles according to the invention can preferably be magnetized more quickly.

FIG. 1 illustrates the isolation of nucleic acids from a sample containing cells. The sample (specimen) that contains cells is pretreated in a sample-specific fashion so that the cells in which the nucleic acids are to be detected are present in the proper form.

When samples are used from which bodily fluids were removed, for instance, this entails adding reagents, e.g., to liquify viscous samples such as saliva. An antibody bound to a solid phase, preferably a bead, that can detect and bind the cell is added to a vessel containing the sample treated in this fashion. Antigens on the cell surface have proven to be suitable partners for the antibody, for instance. The specificity of the antibody can depend on the specificity of the analysis to be performed. If the solid phase is the wall of the vessel, the cells are bound directly to the wall. If the solid phase is comprised of beads, they are separated from the fluid using suitable separation methods. This can be performed by means of filtration, for instance. If magnetic beads are used, they can be separated out by applying a magnetic field to the outside wall of the vessel. The separated cells are washed with a fluid to remove contaminants (that would interfere with the detection) along with the medium surrounding the cells. The conditions are preferably such that the cells are neither separated from the solid phase nor destroyed. The cells are then destroyed, i.e., lysed. This can be performed, for instance, by treating the cells with chaotropic salts. Other possibilities include the application of proteinases and detergents.

In the preferred embodiment, the particles according to the invention are added to the lysis mixture. After a suitable period of time for the lysis to take place—which can be optimized by loading the surface with nucleic acids—the particles are separated from the surrounding fluid that contains additional cell components that are not to be detected. This is performed preferably by applying a magnetic field by placing a magnet against the vessel wall.

To remove any contaminants that may still be present, a wash step is preferably performed with a fluid that does not cause the nucleic acids to be determined to be separated from the glass surface. An elution buffer having reagent conditions under which the nucleic acids separate from the glass surface is added to remove the nucleic acids from the glass surface. These conditions are low salt conditions in particular. Depending on the intended further use of the nucleic acids, the fluid can now be separated from the particles and processed further. This separation step is preferably performed via application of a magnetic field so that the particles are separated from each other.

The following examples explain the invention in greater detail.

EXAMPLE 1

Manufacture of the Magnetic Particles According to the Invention

Six different sols were used. The sols were manufactured as follows:

Sol 1 ($SiO_2$:$B_2O_3$=7:3):
Synthesis was performed in a 250 ml round flask while stirring constantly.
86.6 ml tetraethyl orthosilicate
+7 ml anhydrous, non-denatured ethanol
+14.1 ml 0.15 M HCl A biphasal mixture is produced. Stir it at room temperature until it becomes a single phase. Add dropwise
+37.8 ml trimethylborate
then keep the sol at 50° C. for 2 hours. Add
+14.1 ml 0.15 M HCl Sol 2 ($SiO_2$:$B_2O_3$=4:1):
Synthesis was performed in a 250 ml round flask while stirring constantly.
100.5 ml tetraethyl orthosilicate
+7 ml anhydrous, non-denatured ethanol
+16.3 ml 0.15 M HCl A biphasal mixture is produced. Stir it at room temperature until it becomes a single phase. Add dropwise
+25.6 ml trimethylborate
then keep the Sol at 50° C. for 2 hours. Add
+16.3 ml 0.15 M HCl Sol 3 ($SiO_2$:$B_2O_3$=85:15):
Synthesis was performed in a 250 ml round flask while stirring constantly.
107.8 ml tetraethyl orthosilicate
+7 ml anhydrous, non-denatured ethanol
+17.5 ml 0.15 M HCl A biphasal mixture is produced. Stir it at room temperature until it becomes a single phase. Add dropwise
+19.4 ml trimethylborate
then keep the sol at 50° C. for 2 hours. Add
+17.5 ml 0.15 M HCl Sol 4 ($SiO_2$:$B_2O_3$=4:1; 2 Mol % $P_2O_5$):
Synthesis was performed in a 250 ml round flask while stirring constantly.
100.5 ml tetraethyl orthosilicate
+7 ml anhydrous, non-denatured ethanol
+16.3 ml 0.15 M HCl A biphasal mixture is produced. Stir it at room temperature until it becomes a single phase. Add dropwise
+25.6 ml trimethylborate
then keep the sol at 50° C. for 2 hours. Add
+16.3 ml 0.15 M HCl
+1.63 g $P_2O_5$ Sol 5 ($SiO_2$:$B_2O_3$=4:1 Mol % $Al_2O_3$):
Synthesis was performed in a 250 ml round flask while stirring constantly.
100.5 ml tetraethyl orthosilicate
+7 ml anhydrous, non-denatured ethanol
+16.3 ml 0.15 M HCl A biphasal mixture is produced. Stir it at room temperature until it becomes a single phase. Add dropwise
+25.6 ml trimethylborate
then keep the sol at 50° C. for 2 hours. Add
+16.3 ml 0.15 M HCl
+3.06 g $AlCl_3$ Sol 6 ($SiO_2$:$B_2O_3$=4:1 Mol % $ZrO_2$):
Synthesis was performed in a 250 ml round flask while stirring constantly.
100.5 ml tetraethyl orthosilicate
+7 ml anhydrous, non-denatured ethanol
+16.3 ml 0.15 M HCl A biphasal mixture is produced. Stir it at room temperature until it becomes a single phase. Add dropwise
+25.6 ml trimethylborate
+5.15 ml zircon(IV)-proylate, 70% solution by weight in 1-propanol
then keep the sol at 50° C. for 2 hours. Add
+16.3 ml 0.15 M HCl After another 2 hours at 50° C., 22.5 g Iriodin 600 (black mica) was added for each 150 ml sol and stirred. It was then coated with a spray dryer (Büchi 190, Mini Spray Dryer).

The temperature of the spray dryer nozzle was 134° C. The powder obtained in the spray drying process was then subjected to a temperature treatment step in a nitrogen atmosphere (90 l/h). The temperature was increased at a rate of 1 k/min and the powder was maintained at a densification temperature for 2 hours. For coating with sol $_1$, this temperature was 750° C., and 860° C. for coating with sol 2. The temperature was 800° C. for all other coating processes. After the sintering process the oven was turned off and the powder was brought to room temperature. Agglomerates were sifted out using a 50 μm sieve.

EXAMPLE 2

Manufacture of GMP1, GMP2, GMP3 and GMP4

GMP1, GMP2, GMP3 and GMP4 are pigments from different production lots that were obtained from sol 1 (example 1) in a process described in example 1, under the following conditions:

| Parameter | GMP 1 | GMP 2 | GMP 3 | GMP 4 |
|---|---|---|---|---|
| Aging of the sol (h) (30° C.) | 36 | 36 | 36 | 36 |
| Percentage of pigment in sol (g/100 ml) | 5 | 15 | 8 | 20 |
| Nozzle air flow (%) | 100 | 100 | 100 | 100 |
| Air pressure (bar) | 6 | 6 | 6 | 3 |
| Nozzle temperature (° C.) | 135 | 120 | 130 | 143 |
| Densification temperature (° C.) | 534 | 534 | 534 | 615 |
| subsequent $O_2$-treatment (1 hour) | (300° C.) | (300° C.) | (300° C.) | (400° C.) |
| Pigment yield | low | high | medium | high |
| DNA yield | low | high | high | high |

EXAMPLE 3

PCR Sample Pretreatment from Human Whole Blood Using Magnetic Glass Particles

Nucleic Acid Isolation 10 mg each from 3 lots of glass magnetic particles (GMP 2-4) were placed in Eppendorf test tubes. The exact sample weights are indicated in Table 1. Three-fold determinations were performed.

40 µl proteinase K (20 mg/ml, made from lyophilisate) were added via pipetting to each 200 µl of thawed whole blood and mixed immediately. In the next step, 200 µl binding buffer (6 M guanidine-HCl, 10 mM Tris-HCl, 10 mM urea, 30% Triton X-100, pH 4.4) were added, mixed, and then incubated for 10 minutes at 70° C. 200 µl i-propanol were added, and the preparation was then mixed on the vortex mixer for 10 seconds. The sample was left at room temperature for 20 minutes, then mixed once more for 10 seconds. The magnetic separation step was performed for at least 30 seconds in a magnetic particle separator from Boehringer Mannheim (ID# 1 641 794). The supernatant was removed and analyzed as described below.

The magnetic particles were washed with 500 µl wash buffer (20 mM NaCl, 10 mM Tris-HCl, pH 7.5 (25° C.), 80% ethanol) by mixing for 10 seconds, leaving them at room temperature for 1 minute, then mixing for 10 seconds. They were then pulled to the vessel wall using the magnetic particle separator. The supernatant was removed and discarded. The wash procedure was repeated until the wash fluid was colorless (4 times in all). The nucleic acids were then eluted 3× with 200 µl each time of elution buffer prewarmed to 70° C. (10 mM Tris-HCl, pH 8.5), then mixed for 10 seconds, left at room temperature for 10 minutes, and mixed for 10 minutes.

Preparing the Supernatant

The supernatant obtained after the first binding to the magnetic glass particles was investigated as follows for its nucleic acid content: the supernatant was placed in a filter tube (Boehringer Mannheim ID# 1744003, as provided in the High Pure PCR Product Purification Kit, for instance) and centrifuged for 1 hour at 8000 rpm in an Eppendorf tabletop centrifuge. The flow-through material was discarded and the filter tube was washed 2× with 500 µl wash buffer (centrifugation as described above). The filter tube was centrifuged briefly to dryness, and then eluted with 2×200 µl 1× elution buffer prewarmed to 70° C. by centrifuging once more.

Analyzing the Eluate and Sample Supernatant

10 µl of sample buffer were added to 50 µl of the eluate and the supernatant prepared using the filter tube, respectively. 45 µl of this preparation were separated in an 0.8% agarose gel using electrophoresis at 120 V for 90 minutes.

Various dilutions of the eluate and the prepared supernatants were measured using spectroscopy at 260 and 280 nm in a Uvikon 710 (Kontron).

Two 5 µl aliquots of eluate were investigated in duplicate determinations using Expand™ Long Template PCR (Boehringer Mannheim ID# 1681834) with specific primers for the human tPA gene (expected length of product: 15 kb).

| Mix I | per batch | Mix II | per batch |
|---|---|---|---|
| dNTP, 100 mM each | 1 µl | Expand ™ buffer, 10× | 5 µl |
| Primer 1, 200 ng/ml | 1 µl | Expand ™ polymerase | 0.75 µl |
| Primer 2, 225 ng/ml | 1 µl | H2O, bidistilled | 19.25 µl |
| H2O, bidistilled | 17 µl | | |
| | 20 µl | | 25 µl |

Mix I is placed in a thin-walled PCR tube with 5 µl eluate, then mix II is added. The preparation is mixed briefly, then covered with a layer of 30 µl of mineral oil. The preparations are amplified in a Perkin Elmer thermal cycler 9600 with the following settings:

| | | |
|---|---|---|
| 2 minutes | 92° C. | |
| 10 seconds | 92° C. | 10 cycles |
| 30 seconds | 65° C. | |
| 12 minutes | 68° C. | |
| 10 seconds | 92° C. | 20 cycles |
| 30 seconds | 65° C. | |
| 12 minutes + 20 seconds per cycle | 68° C. | |
| 7 minutes | 68° C. | |
| then | 7° C. | |

10 µl sample buffer were added to the 50 µl PCR preparations. 45 µl of this mixture were than separated in an 0.8% agarose gel using electrophoresis at 120 V for 90 minutes.

TABLE 1

Yield of nucleic acids using magnetic glass particles and 200 µl blood
Results

| | | | Supernatant 1:8 | | | | 1. Eluate 1:8 | | | |
|---|---|---|---|---|---|---|---|---|---|---|
| | | | 260 nm | 280 nm | Yield | 260/280 | 260 nm | 280 nm | Yield | 260/280 |
| GMP/2 | 12 mg | 1 | 0.021 | 0.013 | 1.7 µg | 1.6 | 0.171 | 0.164 | 13.7 µg | 1.0 |
| | 10 mg | 2 | 0.045 | 0.035 | 3.7 µg | 1.3 | 0.137 | 0.138 | 11.0 µg | 1.0 |
| | 9 mg | 3 | 0.036 | 0.027 | 2.9 µg | 1.3 | 0.153 | 0.164 | 12.2 µg | 0.9 |
| GMP/3 | 10 mg | 1 | 0.050 | 0.042 | 4.0 µg | 1.2 | 0.245 | 0.246 | 19.6 µg | 0.9 |
| | 10 mg | 2 | 0.033 | 0.022 | 2.6 µg | 1.5 | 0.397 | 0.398 | 31.8 µg | 1.0 |
| | 10 mg | 3 | 0.042 | 0.030 | 3.4 µg | 1.4 | 0.278 | 0.282 | 22.2 µg | 0.9 |
| GMP/4 | 10 mg | 1 | 0.065 | 0.056 | 0.7 µg | 1.2 | 0.135 | 0.142 | 11.0 µg | 1.0 |
| | 11 mg | 2 | 0.071 | 0.142 | 2.4 µg | 0.5 | 0.140 | 0.142 | 11.2 µg | 1.0 |
| | 10 mg | 3 | 0.066 | 0.051 | 1.7 µg | 1.3 | 0.130 | 0.130 | 10.4 µg | 1.0 |

TABLE 1-continued

Yield of nucleic acids using magnetic glass particles and 200 μl blood
Results

| | | 2. Eluate 1:8 | | | | 3. Eluate 1:4 | | | | |
|---|---|---|---|---|---|---|---|---|---|---|
| | | 260 nm | 280 nm | Yield | 260/280 | 260 nm | 280 nm | Yield | 260/280 | Σ Eluate |
| GMP/2 | 1 | 0.099 | 0.101 | 7.9 μg | 1.0 | 0.057 | 0.062 | 2.3 μg | 0.9 | 23.9 μg |
| | 2 | 0.078 | 0.076 | 6.2 μg | 1.0 | 0.041 | 0.049 | 1.6 μg | 0.8 | 18.8 μg |
| | 3 | 0.103 | 0.112 | 8.2 μg | 0.9 | miss | | | | |
| GMP/3 | 1 | 0.147 | 0.147 | 11.8 μg | 1.0 | 0.084 | 0.098 | 3.4 μg | 0.9 | 34.8 μg |
| | 2 | 0.256 | 0.252 | 20.5 μg | 1.0 | 0.042 | 0.043 | 1.7 μg | 1.0 | 54.0 μg |
| | 3 | 0.147 | 0.143 | 11.8 μg | 1.0 | 0.073 | 0.093 | 2.9 μg | 0.8 | 36.9 μg |
| GMP/4 | 1 | 0.106 | 0.108 | 8.5 μg | 1.0 | 0.083 | 0.098 | 3.3 μg | 0.8 | 22.8 μg |
| | 2 | 0.111 | 0.114 | 8.9 μg | 1.0 | 0.054 | 0.063 | 2.2 μg | 0.9 | 22.3 μg |
| | 3 | 0.135 | 0.141 | 10.8 μg | 1.0 | 0.077 | 0.095 | 3.1 μg | 0.8 | 24.3 μg |

The first eluates were still slightly yellow in color and slightly contaminated with fine magnetic particles.

The analysis of the eluates in agarose gel (FIG. 2) reveals good reproducibility of the yield. The magnetic particles GMP 2-4 show no significant differences. Eluates 1 (above) an 2 (below) contain approximately the same concentration of nucleic acids (estimated by the gel). Eluate 3 has a low concentration of nucleic acids. The supernatants also contain a low concentration of nucleic acids.

The Expand™PCR yields very good, specific amplification products for all samples, with just a few outliers (Table 2). When magnetic glass beads are used, nucleic acids are isolated from human blood samples that then yielded specific amplificates in a subsequent PCR step.

TABLE 2

Results with Expand ™ PCR

| | | 15 kb Expand ™ PCR | | Human tPA Gene | |
|---|---|---|---|---|---|
| | | 1st Eluate | | | 2nd Eluate |
| GMP/2 | 1 | n/a | | + | + |
| | 2 | + | + | + | + |
| | 3 | + | + | | n/a |
| GMP/3 | 1 | + | + | + | + |
| | 2 | (+) | + | + | + |
| | 3 | − | (+) | + | + |
| GMP/4 | 1 | + | + | + | + |
| | 2 | + | + | + | (+)* |
| | 3 | + | + | | n/a |

K, BM Control DNA
*3rd eluate

FIG. 3 shows a gel with the reaction products after PCR amplification. MWM III is a moleular weight marker (eluate 1, above; eluate 2, below).

EXAMPLE 4

Binding of DNA Length Standard to Magnetic Glass Particles

1. Preparation of the Magnetic Glass Particles
12 mg of glass magnetic particles from GMP 4 are placed in a 12 mg Eppendorf test tube.

2. Lysis and Binding
900 μl lysis buffer (4.6 M GuSCN, 45 mM Tris, 20 EDTA, pH 7.3) and 100 μl DNA sample in which DNA length standard III from Boehringer Mannheim (Cat. No. 528552) was added as a model are mixed in a 1.5 ml Eppendorf vessel with 12 mg magnetic glass particles for 2 to 10 seconds until a homogenous suspension is obtained. The solution is incubated at room temperature for 20 minutes and mixed every 5 minutes. Magnetic separation is performed for at least 15 seconds in a magnetic particle separator. The supernatant is removed via pipetting.

3. Washing and Drying

The magnetic glass particles are washed twice with wash buffer (5.2 M GuSCN, 50 mM Tris, pH 6.5), twice with 70% precooled ethanol, and once with acetone by removing the magnetic field, adding 800 μl solution via pipetting, mixing for 2 seconds, leaving at RT for 1 minutes, applying the magnetic field and then removing the supernatant via pipetting.

When the acetone is removed, the particles are dried for 10 minutes at 56° C. in the heating block with the cover open.

4. Eluting the DNA

The DNA is eluted with 4×50 μl elution buffer (10 mM Tris-HCl, 1 mM EDTA, pH 8.0) by incubating it at 56° C. for 10 minutes while shaking repeatedly. The supernatant, which contains the DNA, is then transferred to a new Eppendorf vessel via pipette.

5. Analyzing the Eluate

Sample buffer is added to one-fifth of the eluate volume and the DNA is separated on a 1% agarose gel at 90 V. To determine the recovery, a dilution series of DNA length standard III is applied to the same gel that contains the quantities of DNA expected in the sample.

The quantitative evaluation is performed by scanning a Polaroid photo of the agarose gel. The dilution series of the standard is used as the calibrator.

The yield of DNA using magnetic glass particles is shown in Table 1.

TABLE 1

Yield of DNA length standard III with magnetic glass particles

| Standard No. | DNA - amount in the standard [ng] | Intensity. Standard (measured) [rel. Units] | Sample no. | Type of pigment/ bead | Intensity sample (measured) [rel.Units] | calculated amount of DNA- in the gel [ng] | calculated amount of DNA in the sample [ng] | Recovery [%] |
|---|---|---|---|---|---|---|---|---|
| 1 | 200 | 65 | 1 | GMP4 | 45 | 139 | 695 | 69.5 |
| 2 | 175 | 56 | 2 | GMP4 | 39 | 120 | 600 | 60.0 |
| 3 | 150 | 51 | | | | | | |
| 4 | 125 | 44 | | | | | | |
| 5 | 100 | 37 | | | | | | |
| 6 | 75 | 25 | | | | | | |
| 7 | 50 | 17 | | | | | | |
| 8 | 25 | 9 | | | | | | |
| 9 | 10 | 4 | | | | | | |

Figure 4:
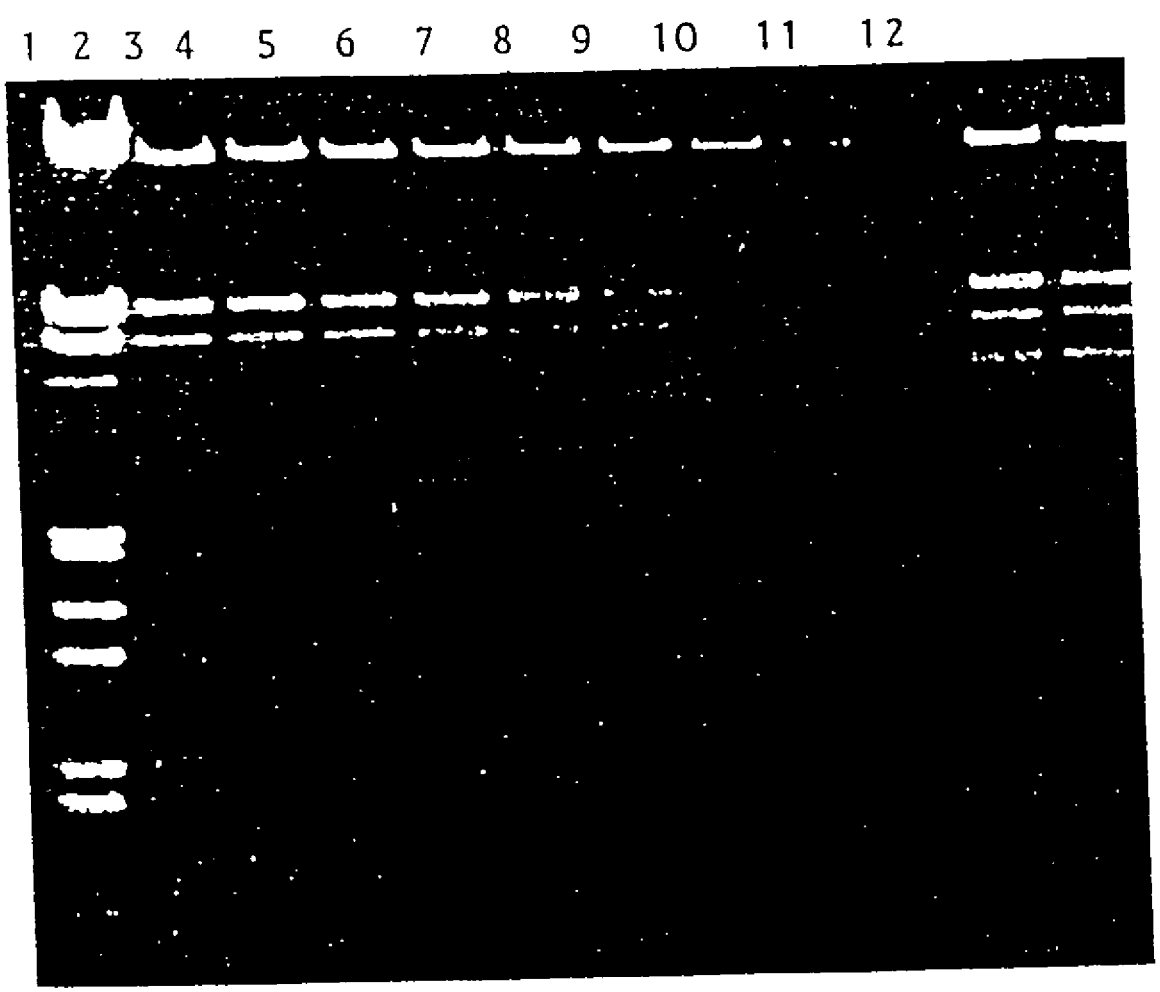
FIG. 4 shows a gel with the results from example 4.

The agarose gel that was used as the basis for the quantitative evaluation is shown in FIG. 4. It is a 1% ethidium bromide-stained agarose gel. Lanes 1 through 10 correspond to a dilution series of DNA length standard III. 1:1 µg DNA, 2: 200 ng DNA, 3: 175 ng DNA, 4: 150 ng DNA, 5: 125 ng DNA, 6: 100 ng DNA, 7: 75 ng DNA, 8: 50 ng DNA, 9: 25 ng DNA, 10: 10 DNA.

Lanes 11 and 12 correspond to the DNA eluted from the magnetic glass particles with 200 ng DNA length standard added.

Sequence Protocol
(1) GENERAL INFORMATION:
(i) APPLICANT:
(A) NAME: Boehringer Mannheim GmbH
(B) STREET: Sandhoferstr. 116
(C) CITY: Mannheim
(D) COUNTRY: DE
(E) POSTAL CODE: 68298
(F) TEL.: 0621 759 4348
(G) FAX: 0621 759 4457
(ii) NAME OF THE INVENTION: Magnetic Pigment
(iii) NUMBER OF SEQUENCES: 2
(iv) COMPUTER-READABLE FORM:
(A) DATA CARRIER: Floppy disk
(B) COMPUTER: IBM PC Compatible
(C) OPERATING SYSTEM: PC-DOS/MS-DOS
(D) SOFTWARE: Patentin Release #1.0, Version #1.30 (EPA)
(2) INFORMATION ON SEQ ID# 1:
(i) SEQUENCE IDENTIFICATION:
(A) LENGTH: 34 base pairs
(B) TYPE: Nucleotide
(C) STRAND TYPE: Single
(D) TOPOLOGY: Linear
(ii) MOLECULE TYPE: Other nucleic acid
(A) DESCRIPTION: /desc=oligodeoxyribonucleotide
(iii) HYPOTHETICAL: NO
(xi) SEQUENCE DESCRIPTION: SEQ ID NO: 1: ACTGTGCTTC TTGACCCATG GCAGAAGCGC CTTC 34
(2) INFORMATION ON SEQ ID NO: 2:
(i) SEQUENCE IDENTIFICATION:(A) LENGTH: 34 base pairs
(B) TYPE: Nucleotide
(C) STRAND TYPE: Single
(D) TOPOLOGY: Linear
(ii) MOLECULE TYPE: Other nucleic acid
(A) DESCRIPTION: /desc="oligodeoxyribonucleotide"
(iii) HYPOTHETICAL: NO
(xi) SEQUENCE DESCRIPTION: SEQ ID NO: 2: CCTTCACTGT CTGCCTAACT CCTTCGTGTG TTCC 34

The invention claimed is:

1. A method for separating a biological material from a fluid containing the biological material comprising:
   a) bringing a sample that contains the biological material in a fluid in contact with a magnetic particle, the magnetic particle comprising a magnetic core and an outer glass layer, wherein said outer glass layer comprises boron oxide, said outer glass layer completely covers the magnetic core and has an outer glass surface, under conditions such that the biological material binds to the glass surface; and thereafter
   b) separating the bound biological material from the fluid.

2. The method of claim 1, wherein the bound biological material is separated from the fluid using a magnetic field.

3. The method of claim 1, wherein the particle is not subjected to the influence of a magnetic field before being brought in contact with the sample and is thus able to sediment when brought in contact with the sample.

4. The method of claim 1, wherein any pores in the outer glass surface have a diameter of less than 1 mm.

* * * * *

UNITED STATES PATENT AND TRADEMARK OFFICE
CERTIFICATE OF CORRECTION

PATENT NO. : 7,371,830 B2  Page 1 of 1
APPLICATION NO. : 11/041750
DATED : May 13, 2008
INVENTOR(S) : Kleiber et al.

It is certified that error appears in the above-identified patent and that said Letters Patent is hereby corrected as shown below:

Col. 18, line 16-17;
Claim 4 should be corrected:

4. The method of claim 1, wherein any pores in the outer glass surface have a diameter of less than 1 ~~mm~~ nm.

Signed and Sealed this

Fifth Day of August, 2008

JON W. DUDAS
*Director of the United States Patent and Trademark Office*

```
                        SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Oligodeoxyribonucleotide

<400> SEQUENCE: 1
actgtgcttc ttgacccatg gcagaagcgc cttc                              34

<210> SEQ ID NO 2
<211> LENGTH: 34
<212> TYPE: DNA
<213> ORGANISM: Artificial Sequence
<220> FEATURE:
<223> OTHER INFORMATION: Oligodeoxyribonucleotide
```

-continued

```
<400> SEQUENCE: 2
ccttcactgt ctgcctaact ccttcgtgtg ttcc                              34
```